United States Patent [19]

Okamoto et al.

[11] 4,125,604

[45] *Nov. 14, 1978

[54] N2-ARYLSULFONYL-L-ARGININAMIDES AND THE PHARMACEUTICALLY ACCEPTABLE SALTS THEREOF

[75] Inventors: Shosuke Okamoto, 15-18, Asahigaoka 3-chome, Tarumi-ku, Kobe-shi, Hyogo, Japan; Akiko Hijikata, Kobe, Japan; Ryoji Kikumoto, Machida, Japan; Yoshikuni Tamao, Yokohama, Japan; Kazuo Ohkubo, Machida, Japan; Tohru Tezuka, Yokohama, Japan; Shinji Tonomura, Tokyo, Japan

[73] Assignees: Mitsubishi Chemical Industries Limited, Tokyo; Shosuke Okamoto, Hyogo, both of Japan

[*] Notice: The portion of the term of this patent subsequent to Oct. 25, 1994, has been disclaimed.

[21] Appl. No.: 804,334

[22] Filed: Jun. 7, 1977

Related U.S. Application Data

[63] Continuation-in-part of Ser. No. 653,217, Jan. 28, 1976, Pat. No. 4,055,651, and Ser. No. 713,486, Aug. 11, 1976, Pat. No. 4,073,914, and Ser. No. 723,474, Sep. 14, 1976, Pat. No. 4,096,235, and Ser. No. 728,051, Sep. 30, 1976, and Ser. No. 760,929, Jan. 19, 1977, and Ser. No. 760,672, Jan. 19, 1977, Pat. No. 4,093,712, and Ser. No. 760,745, Jan. 19, 1977, Pat. No. 4,066,773, and Ser. No. 760,668, Jan. 19, 1977, and Ser. No. 760,676, Jan. 19, 1977.

[51] Int. Cl.$^2$ .................. A61K 37/00; C07C 103/52
[52] U.S. Cl. ..................... 424/177; 560/168; 424/248.5; 546/147; 424/248.52; 424/248.51; 546/206; 562/427; 562/428; 546/203; 562/430; 546/204; 546/205; 544/159; 544/58; 260/112.5 K; 260/306.7 R; 260/307 FA; 260/326.33; 260/347.2; 260/345.8 R; 260/518 R; 260/518 A; 260/519; 424/246; 424/258; 424/267; 424/270; 424/272; 424/274; 424/283; 424/285; 424/309; 424/319; 560/10; 560/153; 560/121; 560/123; 560/124; 560/125
[58] Field of Search ............. 260/112.5 R, 243 R, 260/247.1 R, 283 T, 293.62, 306.7 R, 307 FA, 326.33, 347.2, 345.8, 518 R, 518 A, 519; 424/177, 246, 248, 258, 267, 270, 272, 274, 283, 285, 309, 319; 560/10, 153, 121, 123, 124, 125, 168

[56] References Cited

U.S. PATENT DOCUMENTS 4,046,876  9/1977  Okamoto et al. ................ 424/177

*Primary Examiner*—Delbert R. Phillips
*Attorney, Agent, or Firm*—Oblon, Fisher, Spivak, McClelland & Maier

[57] ABSTRACT

N$^2$-Arylsulfonyl-L-argininamides and the pharmaceutically acceptable salts thereof have been found to be effective as pharmaceutical agents for the inhibition and suppression of thrombosis in mammals.

4 Claims, No Drawings

N2-ARYLSULFONYL-L-ARGININAMIDES AND THE PHARMACEUTICALLY ACCEPTABLE SALTS THEREOF

CROSS-REFERENCE TO RELATED APPLICATIONS

This application is a continuation-in-part of the following prior filed application:
Ser. No. 653,217 of Jan. 28, 1976, U.S. Pat. No. 4,055,651
Ser. No. 713,486 of Aug. 11, 1976, U.S. Pat. No. 4,073,914
Ser. No. 723,474 of Sept. 14, 1976, U.S. Pat. No. 4,096,235
Ser. No. 728,051 of Sept. 30, 1976
Ser. No. 760,929 of Jan. 19, 1977
Ser. No. 760,672 of Jan. 19, 1977, U.S. Pat. No. 4,093,712
Ser. No. 760,745 of Jan. 19, 1977, U.S. Pat. No. 4,066,773
Ser. No. 760,668 of Jan. 19, 1977
Ser. No. 760,676 of Jan. 19, 1977

BACKGROUND OF THE INVENTION

1. Field of the Invention

This invention relates to the discovery of certain new and useful $N^2$-arylsulfonyl-L-argininamides and the pharmaceutically acceptable salts thereof, which are of especial value in view of their outstanding antithrombotic properties and low toxicities.

2. Description of the Prior Art

In the past, there have been many attempts to obtain new and improved agents for the treatment of thrombosis. The $N^2$-(p-tolysulfonyl)-L-arginine esters have been found to be one type of agent which can be used and these have been found to be effective in dissolving blood clots. (U.S. Pat. No. 3,622,615, issued Nov. 23, 1971). One family of compounds which have been found to be particularly useful as highly specific inhibitors of thrombin for the control of thrombosis is the $N^2$-dansyl-L-arginine ester or amide. (Our pending U.S. application Ser. No. 496,939, filed Aug. 13, 1974 now U.S. Pat. No. 3,978,045). However, there is a continuing need for a highly specific inhibitor of thrombin for the control of thrombosis, which exhibits lower toxicity.

SUMMARY OF THE INVENTION

It has now been discovered that $N^2$-arylsulfonyl-L-argininamides exhibit antithrombotic acitivity and even lower toxicity levels at the same relative potencies, as compared with the $N^2$-dansyl-L-arginine ester or amide.

An $N^2$-arylsulfonyl-L-argininamide of the formula (I) having the D-configuration in the carbon atom to which the carboxyl group or the ester thereof is attached:

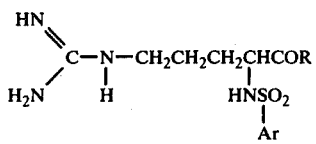

or a pharmaceutically acceptable salt thereof, wherein R is

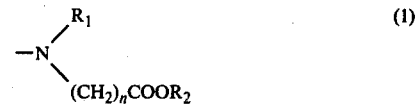

wherein $R_1$ is $C_2$–$C_{10}$ carboxyalkyl, $C_3$–$C_{10}$ alkoxycarbonylalkyl or $C_8$–$C_{15}$ α-carboxyaralkyl; $R_2$ is hydrogen, $C_1$–$C_{10}$ alkyl, $C_6$–$C_{10}$ aryl, $C_7$–$C_{12}$ aralkyl or 5-indanyl; and $n$ is an integer of 1, 2 or 3,

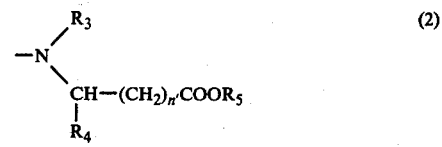

wherein $R_3$ is $C_2$–$C_{10}$ carboxyalkyl, $C_3$–$C_{10}$ alkoxycarbonylalkyl or $C_8$–$C_{15}$ α-carboxyaralkyl; $R_4$ is $C_1$–$C_{10}$ alkyl, phenyl optionally substituted with at least one $C_1$–$C_5$ alkyl, $C_1$–$C_5$ alkoxy, or mixtures thereof, $C_7$–$C_{12}$ aralkyl, or ring substituted benzyl wherein said substituent is $C_1$–$C_5$ alkyl or $C_1$–$C_5$ alkoxy; $R_5$ is hydrogen, $C_1$–$C_{10}$ alkyl, $C_6$–$C_{10}$ aryl, $C_7$–$C_{12}$ aralkyl or 5-indanyl; and $n'$ is an integer of 0, 1 or 2,

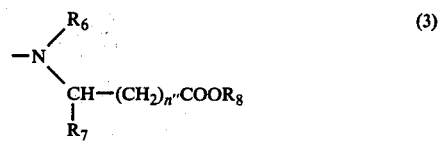

wherein $R_6$ is hydrogen, $C_1$–$C_{10}$ alkyl, $C_3$–$C_{10}$ alkenyl, $C_3$–$C_{10}$ alkynyl, $C_2$–$C_{10}$ alkoxyalkyl, $C_2$–$C_{10}$ alkylthioalkyl, $C_2$–$C_{10}$ alkylsulfinylalkyl, $C_1$–$C_{10}$ hydroxyalkyl, $C_3$–$C_{10}$ alkylcarbonylalkyl, $C_1$–$C_{10}$ haloalkyl, $C_7$–$C_{15}$ aralkyl, $C_3$–$C_{10}$ cycloalkyl, $C_4$–$C_{10}$ cycloalkylalkyl, furfuryl, tetrahydrofurfuryl optionally substituted with at least one $C_1$–$C_5$ alkyl, $C_1$–$C_5$ alkoxy or mixtures thereof, 3-furylmethyl, tetrahydro-3-furylmethyl optionally substituted with at least one $C_1$–$C_5$ alkyl, $C_1$–$C_5$ alkoxy or mixtures thereof, tetrahydro-2 (3 or 4)-pyranylmethyl optionally substituted with at least one $C_1$–$C_5$ alkyl, $C_1$–$C_5$ alkoxy or mixtures thereof, 1,4-dioxa-2-cyclohexylmethyl optionally substituted with one or more $C_1$–$C_5$ alkyl, $C_1$–$C_5$ alkoxy or mixtures thereof, 2-thenyl, 3-thenyl, tetrahydro-2-thenyl optionally substituted with at least one $C_1$–$C_5$ alkyl, $C_1$–$C_5$ alkoxy or mixtures thereof, or tetrahydro-3-thenyl; $R_7$ is carboxyl or $C_2$–$C_{10}$ alkoxycarbonyl; $R_8$ is hydrogen, $C_1$–$C_{10}$ alkyl, $C_6$–$C_{10}$ aryl, $C_7$–$C_{12}$ aralkyl or 5-indanyl; and $n''$ is an integer of 0, 1 or 2,

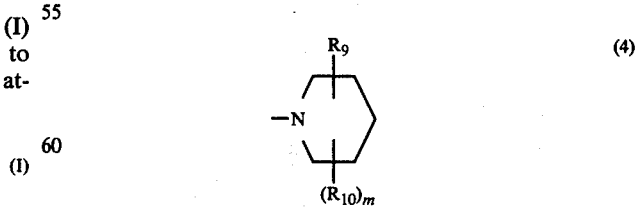

wherein $R_9$ is —$COOR_{11}$ wherein $R_{11}$ is hydrogen, $C_1$–$C_{10}$ alkyl, $C_6$–$C_{10}$ aryl, $C_7$–$C_{12}$ aralkyl or 5-indanyl; each $R_{10}$ independently is hydrogen, $C_1$–$C_{10}$ alkyl, phenyl, $C_1$–$C_5$ alkoxy, $C_2$–$C_6$ alkoxycarbonyl or carboxy; $m$ is an integer of 1 to 4; $R_9$ is substituted at the 2 or 3-position; and $R_{10}$ can be substituted at the 2, 3, 4, 5 or 6-position,

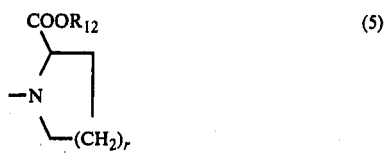 (5)

optionally substituted with at least one $C_1$–$C_5$ alkyl, $C_1$–$C_5$ alkoxy or mixtures thereof wherein $R_{12}$ is hydrogen, $C_1$–$C_{10}$ alkyl, $C_6$–$C_{10}$ aryl, $C_7$–$C_{12}$ aralkyl or 5-indanyl; and $r$ is an integer of 1, 3, 4, 5 or 6.

 (6)

wherein $R_{13}$ is hydrogen, $C_1$–$C_{10}$ alkyl, $C_6$–$C_{10}$ aryl, $C_7$–$C_{12}$ aralkyl or 5-indanyl; Z is oxy, thio or sulfinyl; and $q$ is an integer of 0 or 1, or 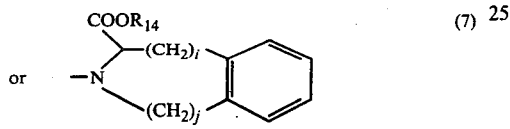 (7)

wherein $R_{14}$ is hydrogen, $C_1$–$C_{10}$ alkyl, $C_6$–$C_{10}$ aryl, $C_7$–$C_{12}$ aralkyl or 5-indanyl; $i$ is an integer of 0, 1 or 2; $j$ is an integer of 0, 1 or 2; and the sum of $i + j$ is an integer of 1 or 2; and Ar is a phenyl, naphthyl, naphthoquinonyl, anthryl, phenanthryl, pentalenyl, heptalenyl, azulenyl, biphenylenyl, as-indacenyl, S-indacenyl, acenaphthylenyl, phenylcarbonylphenyl, phenoxyphenyl, benzofuranyl, isobenzofuranyl, benzo(b)thienyl, isobenzothienyl, oxanthrenyl, thianthrenyl, dibenzofuranyl, dibenzothienyl, phenoxathiinyl, indolyl, 1H-indazolyl, quinolyl, isoquinolyl, phthalazinyl, 1,8-naphthyridinyl, quinoxalinyl, quinazolinyl, cinnolinyl, carbazolyl, acridinyl, phenazinyl, phenothiazinyl, phenoxazinyl or benzimidazolyl group each of which is unsubstituted or substituted with one or more groups selected from the group consisting of halo, nitro, cyano, hydroxy, $C_1$–$C_{10}$ alkyl, $C_1$–$C_{10}$ alkoxy, $C_2$–$C_{20}$ dialkylamino, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl, and phenyl optionally substituted with at least one hydroxy, $C_1$–$C_5$ alkoxy or mixtures thereof, or a $C_9$–$C_{16}$ cycloalkylphenyl, $C_{10}$–$C_{18}$ cycloalkylalkylphenyl, $C_9$–$C_{16}$ cycloalkoxyphenyl, $C_9$–$C_{16}$ cycloalkylthiophenyl, 5,6,7,8-tetrahydronaphthyl, $C_7$–$C_{12}$ aralkyl, 9,10-dihydroanthryl, 5,6,7,8-tetrahydroanthryl, 9,10-dihydrophenanthryl, 1,2,3,4,5,6,7,8-octahydrophenanthryl, indenyl, indanyl, fluorenyl, acenaphthenyl, phenylthiophenyl, 1,2-methylenedioxyphenyl, 1,2-ethylenedioxyphenyl, chromanyl, isochromanyl, 2,3-dihydrobenzofuranyl, 1,3-dihydroisobenzofuranyl, 2,3-ethylenedioxynaphthyl, xanthenyl, thioxanthenyl, 1,2-trimethylenedioxyphenyl, 2H-chromenyl, 3,4-dehydro-1-isochromanyl, 4H-chromenyl, indolinyl, isoindolinyl, 1,2,3,4-tetrahydroquinolyl, or 1,2,3,4-tetrahydroisoquinolyl group each of which is unsubstituted or substituted with one or more groups selected from the group consisting of halo, nitro, cyano, hydroxy, $C_1$–$C_{10}$ alkyl, $C_1$–$C_{10}$ alkoxy, $C_2$–$C_{20}$ dialkylamino, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl, oxo and phenyl optionally substituted with at least one hydroxy, $C_1$–$C_5$ alkoxy or mixtures thereof.

Also encompassed within this invention are pharmaceutically acceptable salts thereof.

This invention also relates to a method for inhibiting activity and suppressing activation of thrombin in vivo in mammals which comprises administering to a mammal a pharmaceutically (antithrombotically) effective amount of an $N^2$-arylsulfonyl-L-argininamide or the pharmaceutically acceptable salts thereof.

DETAILED DESCRIPTION OF THE PREFERRED EMBODIMENTS

This invention relates to a group of $N^2$-arylsulfonyl-L-argininamides of the formula (I) having the D-configuration in the carbon atom to which the carboxyl group or the ester thereof is attached:

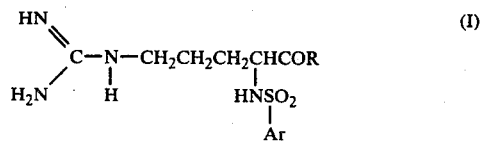 (I)

wherein R is selected from the group consisting of

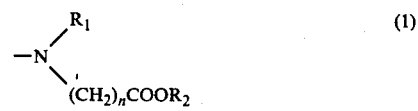 (1)

wherein $R_1$ is selected from the group consisting of carboxyalkyl of 2–10 (preferably 2–7) carbon atoms, such as carboxymethyl, 2-carboxyethyl, 2-carboxypropyl, 3-carboxypropyl, 1-carboxybutyl, 2-carboxybutyl, 4-carboxybutyl or the like, alkoxycarbonylalkyl of 3–10 (preferably 3–8) carbon atoms, such as methoxycarbonylmethyl, 2-ethoxycarbonylethyl, 2-ethoxycarbonylpropyl, 3-methoxycarbonylpropyl, 1-methoxycarbonylbutyl, 2-ethoxycarbonylbutyl, 4-methoxycarbonylbutyl or the like, and α-carboxyaralkyl of 8–15 (preferably 8–12) carbon atoms, such as α-carboxybenzyl, α-carboxyphenethyl or the like; $R_2$ is selected from the group consisting of hydrogen, $C_1$–$C_{10}$ alkyl, such as methyl, ethyl, propyl, butyl, tert-butyl, hexyl, octyl, decyl or the like, $C_6$–$C_{10}$ aryl, such as phenyl, m-tolyl, naphthyl or the like, aralkyl of 7–12 (preferably 7–10) carbon atoms, such as benzyl, phenethyl or the like, or 5-indanyl; and $n$ is an integer of 1, 2 or 3,

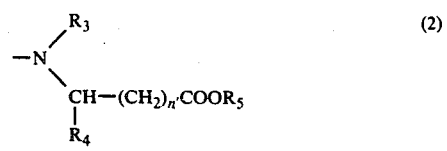 (2)

wherein $R_3$ is selected from the groups consisting of carboxyalkyl of 2–10 (preferably 2–7) carbon atoms, such as carboxymethyl, 2-carboxyethyl, 2-carboxypropyl, 3-carboxypropyl, 1-carboxybutyl, 2-carboxybutyl, 4-carboxybutyl or the like, alkoxycarbonylalkyl of 3-10 (preferably 3-8) carbon atoms, such as methoxycarbonylmethyl, 2-ethoxycarbonylethyl, 2-ethoxycarbonylpropyl, 3-methoxycarbonylpropyl, 1-methoxycarbonylbutyl, 2-ethoxycaarbonylbutyl, 4-methoxycarbonylbutyl or the like, and α-carboxyaralkyl of 8-15 (preferably 8-12) carbon atoms, such as α-carboxybenzyl, α-carboxyphenethyl or the like; $R_4$ is selected from the group consisting of alkyl of 1-10 (preferably 1-5) carbon atoms, such as methyl, ethyl, propyl, isopropyl, butyl, isobutyl, sec-butyl, pentyl or the like, phenyl optionally substituted with one or more $C_1$-$C_5$ alkyl, such as methyl, ethyl, propyl, butyl or the like, and/or $C_1$-$C_5$ alkoxy groups, such as methoxy, ethoxy, propoxy, butoxy or the like, aralkyl of 7-12 (preferably 7-10) carbon atoms, such as benzyl, phenethyl or the like, and ring substituted benzyl wherein said substituent is alkyl of 1-5 (preferably 1-3) carbon atoms, such as methyl, ethyl, propyl or isopropyl, or alkoxy of 1-5 (preferably 1-3) carbon atoms, such as methoxy, ethoxy, propoxy or isopropoxy; $R_5$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10) carbon atoms, such as benzyl, phenethyl or the like, or 5-indanyl; and $n'$ is an integer of 0, 1 or 2,

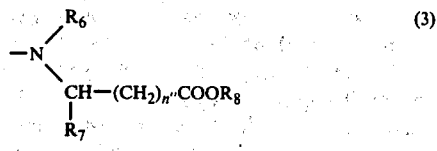

(3)

wherein $R_6$ is hydrogen, $C_1$-$C_{10}$ alkyl, such as methyl, ethyl, propyl, butyl, isobutyl, pentyl, hexyl, octyl, decyl or the like, alkenyl of 3-10 (preferably 3-6) carbon atoms, such as allyl, 2-butenyl, 3-butenyl, 2-pentenyl or the like, alkynyl of 3-10 (preferably 3-6) carbon atoms, such as 2-propynyl, 2-butynyl, 3-butynyl or the like, alkoxyalkyl of 2-10 (preferably 2-6) carbon atoms, such as methoxymethyl, ethoxymethyl, propoxymethyl, 2-methoxyethyl, 2-ethoxyethyl, 2-propoxyethyl, 2-methoxypropyl, 3-methoxypropyl, 3-ethoxypropyl, 3-propoxypropyl, 4-methoxybutyl, 4-ethoxybutyl, 4-butoxybutyl, 5-butoxypentyl or the like, alkylthioalkyl of 2-10 (preferably 2-6) carbon atoms, such as methylthiomethyl, ethylthiomethyl, propylthiomethyl, 2-methylthioethyl, 2-ethylthioethyl, 2-propylthioethyl, 3-methylthiopropyl, 2-methylthiopropyl, 3-ethylthiopropyl, 3-propylthiopropyl, 4-methylthiobutyl, 4-ethylthiobutyl, 4-butylthiobutyl, 5-butylthiopentyl or the like, alkylsulfinylalkyl of 2-10 (preferably 2-6) carbon atoms, such as methylsulfinylmethyl, ethylsulfinylmethyl, propylsulfinylmethyl, 2-methylsulfinylethyl, 2-ethylsulfinylethyl, 2-propylsulfinylethyl, 3-methylsulfinylpropyl, 3-ethylsulfinylpropyl or the like, hydroxyalkyl of 1-10 (preferably 1-6) carbon atoms, such as hydroxymethyl, 2-hydroxyethyl, 3-hydroxypropyl, 2-hydroxypropyl, 4-hydroxybutyl, 3-hydroxybutyl, 5-hydroxypentyl or the like, alkylcarbonylalkyl of 3 to 10 carbon atoms such as methylcarbonylethyl or the like, haloalkyl of 1-10 (preferably 1-5) carbon atoms such as chloromethyl, 2-chloroethyl, 2-bromoethyl, 2-chloropropyl, 3-chloropropyl, 2-chlorobutyl, 4-chlorobutyl or the like, aralkyl of 7-15 (preferably 7-10) carbon atoms, such as benzyl, phenethyl, 3-phenylpropyl, 4-phenylbutyl, 6-phenylhexyl, 1-phenylethyl, 2-phenylpropyl or the like, $C_3$-$C_{10}$ cycloalkyl, such as cyclopropyl, cyclobutyl, cyclopentyl, cyclohexyl, cycloheptyl, cyclooctyl, cyclononyl or cyclodecyl, $C_4$-$C_{10}$ cycloalkylalkyl, such as cyclopropylmethyl, cyclopentylmethyl, cyclohexylmethyl, 2-cyclohexylethyl, cyclooctylmethyl or the like, furfuryl, tetrahydrofurfuryl optionally substituted with one or more $C_1$-$C_5$ alkyl such as methyl, ethyl, propyl, butyl or the like, and/or $C_1$-$C_5$ alkoxy groups, such as methoxy, ethoxy, propoxy, butoxy or the like, 3-furylmethyl, tetrahydro-3-furylmethyl optionally substituted with one or more $C_1$-$C_5$ alkyl such as methyl, ethyl, propyl, butyl or the like, and/or $C_1$-$C_5$ alkoxy groups, such as methoxy, ethoxy, propoxy, butoxy or the like, tetrahydro-2 (3 or 4) -pyranylmethyl optionally substituted with one or more $C_1$-$C_5$ alkyl such as methyl, ethyl, propyl, butyl or the like, and/or $C_1$-$C_5$ alkoxy groups, such as methoxy, ethoxy, propoxy, butoxy or the like, 1,4-dioxa-2-cyclohexylmethyl optionally substituted with one or more $C_1$-$C_5$ alkyl such as methyl, ethyl, propyl, butyl or the like and/or $C_1$-$C_5$ alkoxy groups, such as methoxy, ethoxy, propoxy, butoxy or the like, 2-thenyl, 3-thenyl, tetrahydro-2-thenyl optionally substituted with one or more $C_1$-$C_5$ alkyl such as methyl, ethyl, propyl, butyl or the like, and/or $C_1$-$C_5$ alkoxy groups, such as methoxy, ethoxy, propoxy, butoxy or the like, and tetrahydro-3-thenyl; $R_7$ is selected from the group consisting of carboxy and alkoxycarbonyl of 2-10 (preferably 2-5) carbon atoms, such as methoxycarbonyl, ethoxycarbonyl, propoxycarbonyl or the like; $R_8$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10) carbon atoms, such as benzyl, phenethyl or the like, and 5-indanyl; and $n''$ is an integer of 0, 1 or 2,

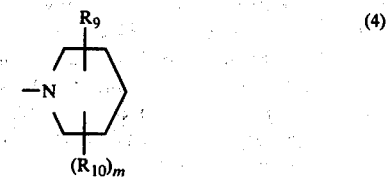

(4)

wherein $R_9$ is —$COOR_{11}$ wherein $R_{11}$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10) carbon atoms, such as benzyl, phenethyl or the like, and 5-indanyl; each $R_{10}$ independently is hydrogen, alkyl of 1-10 (preferably 1-6) carbon atoms, such as methyl, ethyl, propyl, isopropyl, butyl, hexyl, octyl, decyl or the like, phenyl, $C_1$-$C_5$ alkoxy, such as methoxy, ethoxy, propoxy, butoxy or the like, $C_2$-$C_6$ alkoxycarbonyl, such as methoxycarbonyl, ethoxycarbonyl or the like, or carboxy; $m$ is an integer of 1 to 4; $R_9$ is substituted at the 2 or 3-position; and $R_{10}$ can be substituted at the 2, 3, 4, 5 or 6 -position.

(5)

optionally substituted with one or more $C_1$-$C_5$ alkyl, such as methyl, ethyl, propyl, butyl or the like, or $C_1$-$C_5$ alkoxy groups, such as methoxy, ethoxy, propoxy, butoxy or the like wherein $R_{12}$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10) carbon atoms, such as benzyl, phenethyl or the like, and 5-indanyl; and r is an integer of 1, 3, 4, 5 or 6.

(6)

wherein $R_{13}$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10) carbon atoms, such as benzyl, phenethyl or the like, and 5-indanyl; Z is selected from the group consisting of oxy (—O—), thio (—S—) and sulfinyl (—SO—); q is an integer of 0 or 1, and

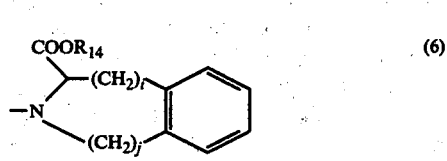

(6)

wherein $R_{14}$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10carbon atoms, such as benzyl, phenethyl or the like, and 5-indanyl; i is an integer of 0, 1 or 2; j is an integer of 0, 1 or 2; and the sum of i + j is an integer of 1 or 2; and Ar is a phenyl, naphthyl, naphthoquinonyl, anthryl, phenanthryl, pentalenyl, heptalenyl, azulenyl, biphenylenyl, as -indacenyl, S-indacenyl, acenaphthylenyl, phenylcarbonylphenyl, phenoxyphenyl, benzofuranyl, isobenzofuranyl, benzo(b)thienyl, isobenzothienyl, oxanthrenyl, thianthrenyl, dibenzofuranyl, dibenzothienyl, phenoxathiinyl, indolyl, 1H-indazolyl, quinolyl, isoquinolyl, phthalazinyl, 1,8-naphthyridinyl, quinoxalinyl, quinazolinyl, cinnolinyl, carbazolyl, acridinyl, phenazinyl, phenothiazinyl, phenoxazinyl or benzimidazolyl group each of which is unsubstituted or substituted with one or more groups selected from the group consisting of halo, nitro, cyano, hydroxy, alkyl of 1-10 (preferably 1-5) carbon atoms, such as methyl, ethyl, propyl, butyl or the like, alkoxy of 1-10 (preferably 1-5) carbon atoms, such as methoxy, ethoxy, propoxy, butoxy or the like, dialkylamino of 2-20 (preferably 2-10) carbon atoms, such as dimethylamino, diethylamino, dipropylamino or the like, sulfoamino, carbamoyl, N,N-dialkylcarbamoyl of 3-10 (preferably 3-7) carbon atoms, such as N,N-dimethylcarbamoyl, N,N-diethylcarbamoyl or the like, amino, alkylamino of 1-10 (preferably 1-5) carbon atoms, such as methylamino, ethylamino, propylamino, butylamino or the like, mercapto, alkylthio of 1-10 (preferably 1-5) carbon atoms, such as methylthio, ethylthio, propylthio, butylthio or the like, aralkyl of 7-12 (preferably 7-10) carbon atoms, such as benzyl, phenethyl or the like, carboxyl, alkoxycarbonyl of 2-10 (preferably 2-6) carbon atoms, such as methoxycarbonyl, ethoxycarbonyl or the like, carboxyalkyl of 2-10 (preferably 2-6) carbon atoms, such as carboxymethyl, 2-carboxyethyl, 2-carboxypropyl or the like, acylamino such as alkylcarbonylamino of 1-10 (preferably 1-5) carbon atoms, such as acetylamino, propionylamino or the like, alkylcarbonyl of 2-10 (preferably 2-6) carbon atoms, such as acetyl, propionyl or the like, hydroxyalkyl of 1-10 (preferably 1-5) carbon atoms, such as hydroxymethyl, 2-hydroxyethyl, 2-hydroxypropyl or the like, haloalkyl of 1-10 (preferably 1-5) carbon atoms, such as chloromethyl, trifluoromethyl, bromomethyl, 2-chloroethyl or the like, and phenyl optionally substituted with at least one hydroxy and/or $C_1$-$C_5$ alkoxy, such as methoxy, ethoxy, propoxy, butoxy or the like; or a $C_9$-$C_{16}$ cycloalkylphenyl, such as cyclopentylphenyl, cyclohexylphenyl, cyclooctylphenyl or the like, $C_{10}$-$C_{18}$ cycloalkylalkylphenyl, such as cyclohexylmethylphenyl, (2-cyclohexylethyl)phenyl, (4-cyclohexylbutyl)phenyl, cyclooctylmethylphenyl or the like, $C_9$-$C_{16}$ cycloalkyloxyphenyl, such as cyclopentyloxyphenyl, cyclohexyloxyphenyl, cyclooctyloxyphenyl or the like, $C_9$-$C_{16}$ cycloalkylthiophenyl, such as cyclopentylthiophenyl, cyclohexylthiophenyl, cyclooctylthiophenyl or the like, 5,6,7,8-tetrahydronaphthyl, $C_7$-$C_{12}$ aralkyl, 9,10-dihydroanthryl, 5,6,7,8-tetrahydroanthryl, 9,10-dihydrophenanthryl, 1,2,3,4,5,6,7,8-octahydrophenanthryl, indenyl, indanyl, fluorenyl, acenaphthenyl, phenylthiophenyl, 1,2-methylenedioxyphenyl, 1,2-ethylenedioxyphenyl, chromanyl, isochromanyl, 2,3-dihydrobenzofuranyl, 1,3-dihydroisobenzofuranyl, 2,3-ethylenedioxynaphthyl, xanthenyl, thioxanthenyl, 1,2-trimethylenedioxyphenyl, 2H-chromenyl, 3,4-dehydro-1-isochromanyl, 4H-chromenyl, indolinyl, isoindolinyl, 1,2,3,4-tetrahydroquinolyl, or 1,2,3,4-tetrahydroisoquinolyl group each of which is unsubstituted or substituted with one or more groups selected from the group consisting of halo, nitro, cyano, hydroxy, alkyl of 1-10 (preferably 1-5) carbon atoms, such as methyl, ethyl, propyl, butyl or the like, alkoxy of 1-10 (preferably 1-5) carbon atoms, such as methoxy, ethoxy, propoxy, butoxy or the like, dialkylamino of 2-20 (preferably 2-10) carbon atoms, such as dimethylamino, diethylamino, dipropylamino or the like, sulfoamino, carbamoyl, N,N-dialkylcarbamoyl of 3-10 (preferably 3-7) carbon atoms, such as N,N-dimethylcarbamoyl, N,N-diethylcarbamoyl or the like, amino, alkylamino of 1-10 (preferably 1-5) carbon atoms, such as methylamino or the like, mercapto, alkylthio of 1-10 (preferably 1-5) carbon atoms, such as methylthio, ethylthio, propylthio, butylthio or the like, aralkyl of 7-12 (preferably 7-10) carbon atoms, such as benzyl, phenethyl or the like, carboxyl, alkoxycarbonyl of 2-10 (preferably 2-6) carbon atoms, such as methoxycarbonyl, ethoxycarbonyl or the like, carboxyalkyl of 2-10 (preferably 2-6) carbon atoms, such as carboxymethyl, 2-carboxyethyl, 2-carboxypropyl or the like, acylamino such as alkylcarbonylamino of 1-10 (preferably 1-5)

carbon atoms, such as acetylamino, propionylamino or the like, alkylcarbonyl of 2-10 (preferably 2-6) carbon atoms, such as acetyl, propionyl, or the like, hydroxyalkyl of 1-10 (preferably 1-5) carbon atoms, such as hydroxymethyl, 2-hydroxyethyl, 2-hydroxypropyl or the like, haloalkyl of 1-10 (preferably 1-5) carbon atoms, such as chloromethyl, trifluoromethyl, bromomethyl, 2-chloroethyl or the like, oxo and phenyl optionally substituted with at least one hydroxy and/or $C_1$-$C_5$ alkoxy, such as methoxy, ethoxy, propoxy, butoxy or the like.

As one skilled in the art can readily appreciate, the carbon atom of the $N^2$-arylsulfonyl-L-argininamides, to which the carboxyl group or the ester thereof is attached can be an asymmetric carbon atom allowing for the existence of two optically active isomers, the D- and L-diastereoisomers, as well as the racemate, DL-mixture.

In accordance with findings concerning the antithrombotic activity of such compounds possessing an asymmetric carbon atom, the compounds of the present invention having the D-configuration are more active than those of the L-configuration and are the preferred compounds.

For the preparation of the compounds of this invention, various methods can be employed depending upon the particular starting materials and/or intermediates involved.

Successful preparation of these compounds is possible by way of several synthetic routes wich are outlined below.

(a) Condensation of an L-argininamide with an arylsulfonyl halide

This process may be illustrated as follows:

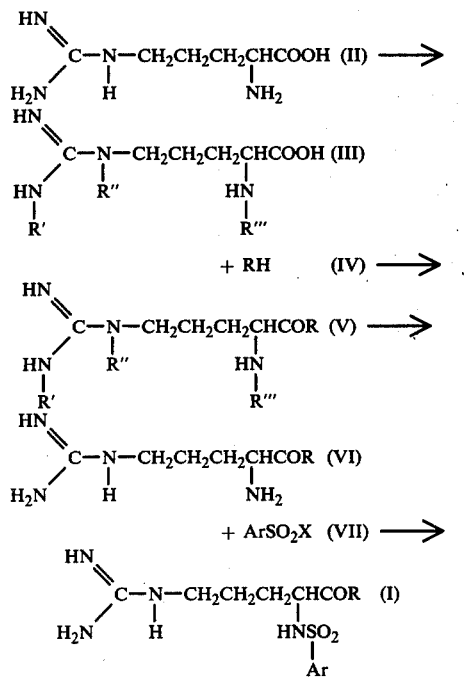

In the above formulas, R and Ar are as defined herein above; X is halogen; R''' is a protective group for the α-amino group, such as benzyloxycarbonyl or tert-butoxycarbonyl; R' and R'' are selected from the group consisting of hydrogen and protective groups for the guanidino group, such as nitro, tosyl, trityl, oxycarbonyl and the like; and at least one of R' and R'' is a protective group for the guanidino group. The $N^2$-arylsulfonyl-L-argininamide (I) is prepared by the condensation of an L-argininamide (VI) with a substantially equimolar amount of an arylsulfonyl halide (VII), preferably a chloride.

The condensation reaction is generally effected in a suitable reaction-inert solvent in the presence of an excess of a base, such as an organic base (triethylamine, pyridine) or a solution of an inorganic base (sodium hydroxide, potassium carbonate), at a temperature of 0° C to the boiling temperature of the solvent for a period of 10 minutes to 15 hours.

The preferred solvents for the condensation include benzene-diethyl ether, diethyl ether-water and dioxane-water.

After the reaction is complete, the formed salt is extracted with water, and the solvent is removed by such standard means as evaporation under reduced pressure to give the $N^2$-arylsulfonyl-L-argininamide (I), which can be purified by trituration or recrystallization from a suitable solvent, such as diethyl ether-tetrahydrofuran, diethyl ether-methanol and water-methanol, or may be chromatographed on silica gel.

The L-argininamides (VI) starting materials required for the condensation reaction can be prepared by protecting the guanidino and α-amino groups of L-arginine (II) via nitration, acetylation, formylation, phthaloylation, trifluoroacetylation, p-methoxybenzyloxycarbonylation, benzoylation, benzyloxycarbonylation, tert-butoxycarbonylation or tritylation and then condensing the formed $N^G$-substituted-$N^2$-substituted-L-arginine (III) with a corresponding amino acid derivative (VI) having the D-configuration in the carbon atom to which the carboxyl group or the ester thereof is attached, by such a conventional process as the acid chloride method, azide method, mixed anhydride method, activated ester method or carbodiimide method, and thereafter selectively removing the protective groups from the formed $N^G$-substituted-$N^2$-substituted-L-argininamide (V).

The amino acid derivatives (IV) which are the starting materials for the preparation of the $N^G$-substituted-$N^2$-substituted-L-argininamides (V) are represented by the following formulas:

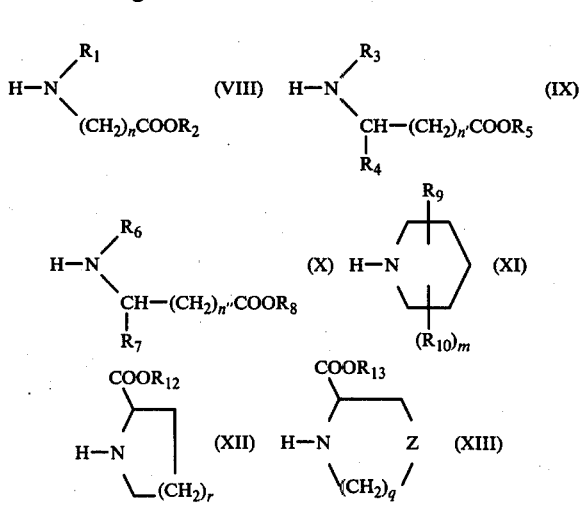

-continued

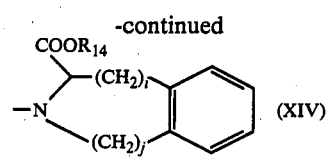

In the above formulas, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$ $n$, $n'$, $n''$, $m$, $r$, $q$, $i$ and $j$ are as defined herein above.

The amino acid derivatives of the above formula (VIII) (IX) or (X) can be prepared by the condensation of a haloacetate, 3-halopropionate or 4-halobutyrate with an appropriate amine having the formula $R_1NH_2$, $R_3NH_2$ or $R_6NH_2$. (See, J. Org. Chem., 25 728-732 (1960)). The condensation reaction is generally carried out without a solvent or in a solvent, such as benzene or ether, in the presence of an organic base, such as triethylamine or pyridine, at a temperature of 0° C to 80° C for a period of 10 minutes to 20 hours. After the reaction is complete, the formed amino acid derivative is separated by such conventional means as extraction with a suitable solvent or evaporation of the reaction solvent and thereafter purified by distillation under reduced pressure.

Among the amino acid derivatives, amino acid tert-butyl ester derivatives are preferred, because they are easily converted to other ester derivatives by acidolysis in the presence of a corresponding alcohol employing an inorganic acid (HCl, $H_2SO_4$, etc.) or an organic acid (toluenesulfonic acid, trifluoroacetic acid, etc.). In accordance with the process employed for preparing 2-piperidinecarboxylic acid derivatives (X), the following scheme is illustrative:

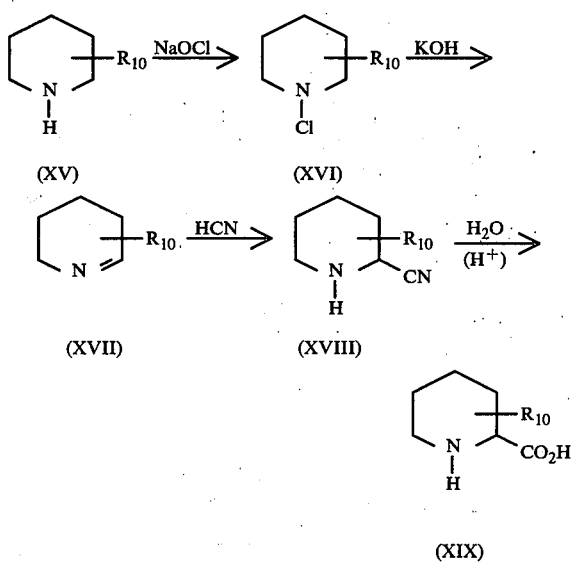

In the first reaction of the aforementioned scheme, an appropriately substituted piperidine (XV) is contacted with an aqueous sodium hypochlorite solution at a temperature of −5° C to 0° C. The resultant product (XVI) is isolated by extraction with a solvent, e.g., diethyl ether, and then treated with potassium hydroxide in a lower alkanol solvent to give the 1,2-dehydropiperidine (XVII). The action of cyanogenating agents, e.g., hydrogen cyanide or sodium cyanide converts the 1,2-dehydropiperidines (XVII) to the corresponding 2-cyano analogs (XVIII). Hydrolysis of the 2-cyanopiperidines (XVIII) to yield the 2-piperidinecarboxylic acids (XIX) is effected by treatment of the 2-cyanopiperidines (XVIII) with an inorganic acid, such as hydrochloric acid or sulfuric acid.

The arylsulfonyl halides (VII) which are the starting materials for the preparation of the $N^2$-arylsulfonyl-L-argininamides (I) can be prepared by halogenating the requisite arylsulfonic acids or their salts, e.g., sodium salts, by conventional methods well known to those skilled in the art.

In practice, halogenation is carried out without a solvent or in a suitable solvent e.g., halogenated hydrocarbons or DMF in the presence of a halogenating agent, e.g., phosphorous oxychloride, thionyl chloride, phosphorous trichloride, phosphorous tribromide or phosphorous pentachloride, at a temperature of −10° C to 200° C for a period of 5 minutes to 5 hours. After the reaction is complete, the reaction product is poured into ice water and then extracted with a solvent such as ether, benzene, ethyl acetate, chloroform or the like.

The arylsulfonyl halide can be purified by recrystallization from a suitable solvent such as hexane, benzene or the like.

(b) Removal of the $N^G$-substituent from an $N^G$-substituted-$N^2$-arylsulfonyl-L-argininamide This process may be illustrated as follows:

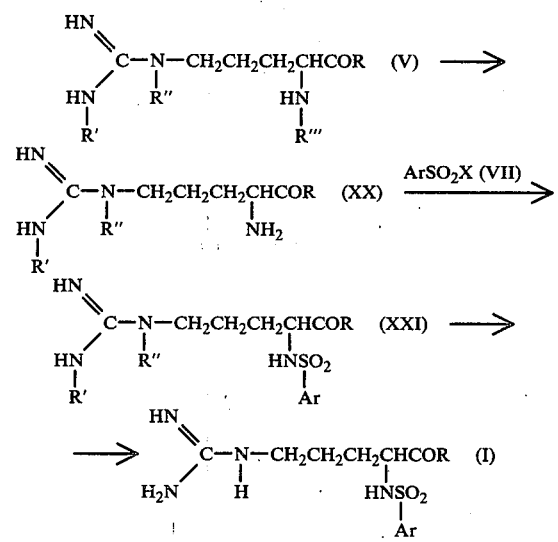

In the above formulas, R, Ar, X, R', R" are R''' are as defined herein above.

The $N^2$-arylsulfonyl-L-argininamide (I) is prepared by removing the $N^G$-substituent from an $N^G$-substituted-$N^2$-arylsulfonyl-L-argininamide (XXI) by means of acidolysis or hydrogenolysis.

The acidolysis is generally effected by contacting the $N^G$-substituted-$N^2$-arylsulfonyl-L-argininamide (XXI) and an excess of an acid such as hydrogen fluoride, hydrogen chloride, hydrogen bromide or trifluoroacetic acid, without a solvent or in a solvent, such as an ether (tetrahydrofuran, dioxane), an alcohol (methanol, ethanol) or acetic acid at a temperature of −10° C to 100° C, and preferably at room temperature for a period of 30 minutes to 24 hours.

The products are isolated by evaporation of the solvent and the excess acid, or by trituration with a suitable solvent followed by filtration and drying.

Because of the use of the excess acid, the products are generally the acid addition salts of the $N^2$-arylsulfonyl-L-argininamides (I), which can be easily converted to a free amide by neutralization.

The removal of the nitro group and the oxycarbonyl group, e.g., benzyloxycarbonyl, p-nitrobenzyloxycarbonyl, is readily accomplished by the hydrogenolysis. At the same time, the benzyl ester moiety which can be included in the R group is converted to the carboxyl group by the hydrogenolysis.

The hydrogenolysis is effected in a reaction-inert solvent, e.g., methanol, ethanol, tetrahydrofuran or dioxane, in the presence of a hydrogen-activating catalyst, e.g., Raney nickel, palladium, or platinum, in a hydrogen atmosphere at a temperature of 0° C to the boiling temperature of the solvent for a period of 2 hours to 120 hours.

The hydrogen pressure is not critical, and atmospheric pressure is sufficient.

The $N^2$-arylsulfonyl-L-argininamides (I) are isolated by filtration of the catalyst followed by evaporation of the solvent.

The $N^2$-arylsulfonyl-L-argininamides can be purified in the same manner as described above.

The $N^G$-substituted-$N^2$-arylsulfonyl-L-argininamides (XXI) starting materials can be prepared by condensing an $N^G$-substituted-$N^2$-substituted-L-arginine (III) (generally the $N^G$-substituent is nitro or acyl, and the $N^2$-substituent is a protective group for the amino group, such as benzyloxycarbonyl, tert-butoxycarbonyl, or the like) and a corresponding amino acid derivative (IV) having the D-configuration in the carbon atom to which the carboxyl group or the ester thereof is attached, selectively removing only the $N^2$-substituent of an $N^G$-substituted-$N^2$-substituted L-argininamide (V) by means of catalytic hydrogenolysis or acidolysis, and then condensing the thus obtained $N^G$-substituted-L-argininamide (XX) with an arylsulfonyl halide (VII), preferably a chloride in the presence of a base in a solvent. These reaction conditions are as described above in the condensation of an L-argininamide with an arylsulfonyl halide, and the removal of the $N^G$-substituent from an $N^G$-substituted-$N^2$-arylsulfonyl-L-argininamide.

(c) Condensation of an $N^2$-arylsulfonyl-L-arginyl halide with an amino acid derivative This process may be illustrated as follows:

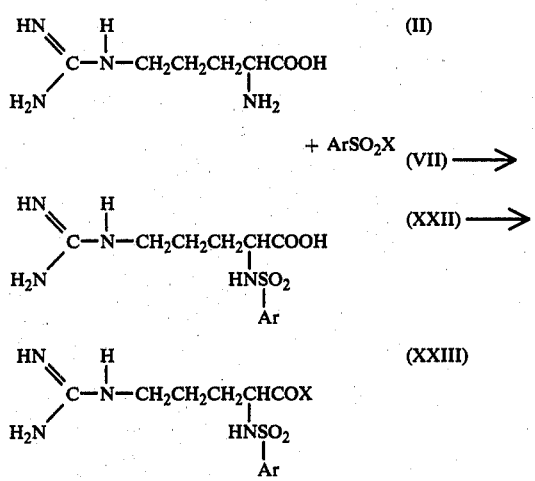

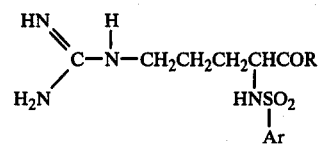

In the above formulas, R, Ar and X are as defined herein above.

The $N^2$-arylsulfonyl-L-argininamide (I) is prepared by the condensation of an $N^2$-arylsulfonyl-L-arginyl halide (XXIII), preferably a chloride with at least an equimolar amount of an amino acid derivative (IV) having the D-configuration in the carbon atom to which the carboxyl group or the ester thereof is attached. The condensation reaction can be carried out without an added solvent in the presence of a base. However, satisfactory results will be obtained with the use of a solvent such as basic solvents (dimethylformamide, dimethylacetamide, etc.) or halogenated solvents (chloroform, dichloromethane, etc.).

The amount of the solvent to be used is not critical and may vary from about 5 to 100 times the weight of the $N^2$-arylsulfonyl-L-arginyl halide (XXIII).

Preferred condensation reaction temperatures are in the range of from $-10°$ C to room temperature. The reaction time is not critical, but varies with the amino acid derivative (IV) employed. In general, a period of from 5 minutes to 10 hours is operable. The obtained $N^2$-arylsulfonyl-L-argininamide can be isolated and purified in the same manner as described above.

The $N^2$-arylsulfonyl-L-arginyl halide (XXIII) starting materials required for the condensation reaction can be prepared by reacting an $N^2$-arylsulfonyl-L-arginine (XXIII) with at least an equimolar amount of a halogenating agent such as thionyl chloride, phosphorous oxychloride, phosphorus trichloride, phosphorous pentachloride or phosphorus tribromide. The halogenation can be carried out with or without an added solvent. The preferred solvents are chlorinated hydrocarbons such as chloroform and dichloromethane, and ethers such as tetrahydrofuran and dioxane.

The amount of the solvent to be used is not critical and may vary from about 5 to 100 times the weight of the $N^2$-arylsulfonyl-L-arginine (XXII).

Preferred reaction temperatures are in the range of $-10°$ C to room temperature. The reaction time is not critical, but varies with the halogenating agent and reaction temperature. In general, a period of 15 minutes to 5 hours is operable.

The $N^2$-arylsulfonyl-L-arginines (XXII) which are the starting materials for the preparation of the $N^2$-arylsulfonyl-L-arginyl halides (XXIII) can be prepared by the condensation of L-arginine (II) with a substantially equimolar amount of arylsulfonyl halides (VII), by a method similar to that described in the condensation of an L-argininamide with an arylsulfonyl halide.

It is well recognized in the art that an ester derivative of the $N^2$-arylsulfonyl-L-argininamide (I) wherein $R_2$, $R_5$, $R_8$, $R_{11}$, $R_{12}$, $R_{13}$ or $R_{14}$ is alkyl, aralkyl, aryl or 5-indanyl, can be prepared from a carboxylic acid derivative of the $N^2$-arylsulfonyl-L-argininamide wherein $R_2$, $R_5$, $R_8$, $R_{11}$, $R_{12}$, $R_{13}$ or $R_{14}$ is hydrogen, by the conventional esterification methods well known to those skilled in the art.

It is also well recognized in the art that the carboxylic acid derivative can be prepared from the ester derivative by the conventional hydrolysis or acidolysis methods. The conditions under which esterification, hydrolysis or acidolysis would be carried out will be each apparent to those skilled in the art.

The $N^2$-arylsulfonyl-L-argininamide (I) of this invention forms acid addition salts with any of a variety of inorganic and organic acids. Some of the $N^2$-arylsulfonyl-L-argininamides containing a free carboxyl group, wherein $R_2$, $R_5$, $R_8$, $R_{11}$, $R_{12}$, $R_{13}$ or $R_{14}$ is hydrogen, forms salts with any of a variety of inorganic and organic bases.

The product of the reactions described above can be isolated in the free form or in the form of salts. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. In a similar manner, the product can be obtained as pharmaceutically acceptable salts by reacting one of the free carboxylic acids with a base, such as sodium hydroxide, potassium hydroxide, ammonium hydroxide, triethylamine, procaine, dibenzylamine, 1-ephenamine, N,N'-dibenzylethylenediamine, N-ethylpiperidine or the like.

Likewise, treatment of the salts with a base or acid results in a regeneration of the free amide.

As stated above, the $N^2$-arylsulfonyl-L-argininamides, and the salts thereof of this invention are characterized by their highly specific inhibitory activity in mammals against thrombin as well as by their substantial lack of toxicity, and therefore these compounds are useful in the determination of thrombin in blood as diagnostic reagents, and/or for the medical control or prevention of thrombosis.

The compounds of this invention are also useful as an inhibitor of platelet aggregation.

The antithrombotic activity of the $N^2$-arylsulfonyl-L-argininamide of this invention was compared with that of a known antithrombotic agent, $N^2$-(p-tolylsulfonyl)-L-arginine methyl ester, by determining the fibrinogen coagulation time. The measurement of the fibrinogen coagulation time was conducted as follows.

An 0.8 ml aliquot of a fibrinogen solution, which had been prepared by dissolving 150 mg of bovine fibrinogen (Cohn fraction I) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath.

Immediately after mixing, the reaction mixture was transferred from the ice bath to a bath maintained at 25° C. Coagulation times were taken as the period between the time of transference to the 25° C bath and the time of the first appearance of fibrin threads. In the cases where no drug samples were added, the coagulation time was 50–55 seconds. The experimental results are summarized in Table 1. The term "concentration required to prolong the coagulation time by a factor of two" is the concentration of an active ingredient required to prolong the normal coagulation time 50–55 seconds to 100–110 seconds.

The concentration required to prolong the coagulation time by a factor of two for the known antithrombotic agent, $N^2$-(p-tolylsulfonyl)-L-arginine methyl ester, was 1,100 μm. The inhibitors are shown in Table 1 by indicating R and Ar in the formula (I) and the addition moiety.

When a solution containing an $N^2$-arylsulfonyl-L-argininamide of this invention was administered intravenously into animal bodies, the high antithrombotic activity in the circulating blood was maintained for from one to three hours.

The halflife for decay of the anti-thrombotic compounds of this invention in circulating blood was shown to be approximately 60 minutes; the physiological conditions of the host animals (rat, rabbit, dog and chimpanzee) were well maintained. The experimental decrease of fibrinogen in animals caused by infusion of thrombin was satisfactorily controlled by simultaneous infusion of the compounds of this invention.

The acute toxicity values ($LD_{50}$) determined by intraperitoneal administration of substances of formula (I) in mice (male, 20 g) range from about 1,000 to 10,000 milligrams per kilogram of body weight.

On the other hand, $LD_{50}$ values for $N^2$-dansyl-N-butyl-L-argininamide and $N^2$-dansyl-N-methyl-N-butyl-L-argininamide are 75 and 70 milligrams per kilogram, respectively.

The therapeutic agents in this invention may be administered to mammals, including humans, alone or in combination with pharmaceutically acceptable carriers, the proportion of which is determined by the solubility and chemical nature of the compound, chosen route of administration and standard pharmaceutical practice.

For example, the compounds may be injected parenterally, that is, intramuscularly, intravenously or subcutaneously. For parenteral administration, the compounds may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents. Physicians will determine the dosage of the present therapeutic agents which will be most suitable for humans, and dosages vary with the mode of administration and the particular compound chosen. In addition, the dosage will vary with the particular patient under treatment.

When the composition is administered orally, a larger quantity of the active agent will be required to produce the same effect as caused with a smaller quantity given parenterally.

The therapeutic dosage is generally 10–50 mg/kg of active ingredient parenterally, 10–500 mg/kg orally per day. Having generally described the invention, a more complete understanding can be obtained by reference to certain specific examples, which are included for purposes of illustration only and are not intended to be limiting unless otherwise specified.

It is to be understood that the present invention includes pharmaceutical compositions containing a compound of the invention as an active ingredient. Such compositions may be in the forms described above. In particular, the invention includes such compositions in unit dose form.

EXAMPLE 1

(A) Benzyl 1-[N$^G$-nitro-N$^2$-(7-methoxy-2-naphthylsulfonyl)-L-arginyl]-L-proline To a well stirred solution of 3.98 g of benzyl 1-(N$^G$-nitro-L-arginyl)-L-proline hydrochloride and 4.15 g of K$_2$CO$_3$ in 15 ml of water and 40 ml of dioxane, was added in portions 5.33 g of 7-methoxy-2-naphthalenesulfonyl chloride, while maintaining the temperature at 0° C. The reaction mixture was stirred overnight at room temperature. At the end of this period, the reaction mixture was evaporated to dryness. The residue was taken up in 50 ml of chloroform, and the chloroform solution was washed consecutively with 10% citic acid, saturated NaCl, saturated NaHCO$_3$ and saturated NaCl solutions. The chloroform solution was evaporated and the residue was chromatographed on silica gel packed in chloroform, and eluted from chloroform containing 3% methanol. The main fraction was evaporated to dryness to give 4.54 g of benzyl 1-[N$^G$-nitro-N$^2$-(7-methoxy-2-naphthylsulfonyl)-L-arginyl]-L-proline.

(B) 1-[N$^2$-(7-methoxy-2-naphthylsulfonyl)-L-arginyl]-L-proline

To a solution of 4.00 g of benzyl 1-[N$^G$-nitro-N$^2$-(7-methoxy-2-naphthylsulfonyl)-L-arginyl]-L-proline in 50 ml of tert-butanol, 5 ml of water and 2 ml of acetic acid, was added 0.2 g of palladium black and then the mixture was shaken in a hydrogen atmosphere for 15 hours at room temperature. The solution was filtered to remove the catalyst and evaporated to give an oily product.

Reprecipitation with ethanol-diethyl ester gave 3.04 g of 1-[N$^2$-(7-methoxy-2-naphthylsulfonyl)-L-arginyl]-L-proline as an amorphous solid.

I.R. (KBr): 3320, 1630, 1160 cm$^{-1}$ $[\alpha]_D$ − 107.6° (C = 1.00, 50% Ethanol)

Analysis — Calcd. for C$_{22}$H$_{29}$O$_6$N$_5$S (percent): C, 53.76; H, 5.95; N, 14.25. Found (percent): C, 53.41; H, 5.76; N, 14.06.

EXAMPLE 2

(A) N$^2$-(6,7-dimethoxy-2-naphthylsulfonyl)-L-arginyl chloride hydrochloride A suspension of 2.00 g of N$^2$-(6,7-dimethoxy-2-naphthylsulfonyl)-L-arginine in 20 ml of thionyl chloride was stirred for 2 hours at room temperature. Addition of cold dry diethyl ether resulted in a precipitate which was collected by filtration and washed several times with dry diethyl ether to give N$^2$-(6,7-dimethoxy-2-naphthylsulfonyl)-L-arginyl chloride hydrochloride.

(B) Ethyl 1-[N$^2$-(6,7-dimethoxy-2-naphthylsulfonyl)-L-arginyl]-L-2-piperidinecarboxylate To a stirred solution of 1.11 g of ethyl-L-2-piperidinecarboxylate and 1.70 ml of triethylamine in 50 ml of chloroform, which was cooled in an ice-salt bath, was added in portions N$^2$-(6,7-dimethoxy-2-naphthylsulfonyl)-L-arginyl chloride hydrochloride obtained above. The reaction mixture was stirred overnight at room temperature. At the end of this period, the chloroform solution was washed twice with 50 ml of saturated sodium chloride solution, dried over Na$_2$SO$_4$ and evaporated in vacuo. The oily residue was washed with ether to give 2.3 g (82%) of powdery ethyl 1-[N$^2$-(6,7-dimethoxy-2-naphthylsulfonyl)-L-arginyl]-L-2-piperidinecarboxylate. For analysis of the product, a portion of the product was converted to the picrate, M.P. 107–110° C I.R. (KBr): 3,425–3,175 (broad), 1,715, 1,610 cm$^{-1}$ Analysis — Calcd. for C$_{26}$H$_{37}$O$_7$N$_5$S.C$_6$H$_3$O$_7$N$_3$ (percent): C, 48.47; H, 5.10; N, 14.14. Found (percent): C, 48.44; H, 5.30; N, 13.75

(C) 1-[N$^2$-(6,7-dimethoxy-2-naphthylsulfonyl)-L-arginyl]-L-2-piperidinecarboxylic acid A solution of 2.00 g of ethyl 1-[N$^2$-(6,7-dimethoxy-2-naphthylsulfonyl)-L-arginyl]-L-2-piperidinecarboxylate in 10 ml of ethanol and 5 ml of 2N-NaOH solution was stirred overnight at room temperature. At the end of this period, the reaction mixture was concentrated and chromatographed on 200 ml of Daiaion ® SK 102 ion exchange resin (200–300 mesh, H$^+$ form, manufactured by Mitsubishi Chemical Industries Limited) packed in water, washed with ethanol-water (1 : 4) and eluted with ethanol-water-NH$_4$OH (10 : 9 : 1). The main fraction was concentrated to ca. 10 ml to give 1.40 g of 1-[N$^2$-(6,7-dimethoxy-2-naphthylsulfonyl)-L-arginyl]-L-2-piperidinecarboxylate acid, M.P. 229°–233° C $[\alpha]_D$ − 33.7° (C = 1.00, 50% Ethanol)

I.R. (KBr): 3,350, 1,620 cm$^{-1}$

Analysis — Calcd. for C$_{24}$H$_{33}$O$_7$N$_5$S.½H$_2$O (percent): C, 52.94; H, 6.30; N, 12.87. Found (percent): C, 52.73; H, 6.15; N, 12.93

Various other N$^2$-arylsulfonyl-L-argininamides or acid addition salts thereof were synthesized in accordance with the procedure of the above examples, and the test results are summarized in Table 1.

TABLE 1

Structure:

$$HN=C(NH_2)-N(H)-CH_2CH_2CH_2-CH(COR)-NH-SO_2-Ar$$

| No. | Ar | R | | Addition moiety | Concentration required to prolong the coagulation time by a factor of two (μM) | Preparation Process (Ex. No.) | m.p. °C | $[\alpha]_D^{25}$ (C = 1.00) (50% EtOH) | Elemental analysis Upper: Calculated Lower: Found C | H | N | I.R. (KBr) cm$^{-1}$ |
|---|---|---|---|---|---|---|---|---|---|---|---|---|
| 1 | 2,3-dimethoxynaphthyl | COOC$_2$H$_5$ piperidine | (L) | picric acid · ½H$_2$O | | 2 | 107–110 | | 48.47 / 48.44 | 5.10 / 5.30 | 14.14 / 13.75 | 3,425 (broad) / 3,175 (broad) / 1,715 / 1,610 |
| 2 | " | COOH piperidine | (L) | picric acid · ½H$_2$O | 15 | 2 | 229–233 | −33.7 | 52.94 / 52.73 | 6.30 / 6.15 | 12.87 / 12.93 | 3,350 / 1,620 |
| 3 | " | COOC$_2$H$_5$ piperidine | (D) | picric acid | | 2 | 108–112 | | 47.39 / 47.72 | 5.23 / 5.15 | 13.82 / 13.67 | 3,450 (broad) / 3,200 (broad) / 1,715 / 1,610 |
| 4 | " | COOH piperidine | (D) | 2H$_2$O | 2 | 2 | 195–198 | −77.2 | 50.42 / 50.48 | 6.54 / 6.16 | 12.25 / 12.31 | 3,320 / 1,620 |
| 5 | 6-methoxynaphthyl | COOH pyrrolidine | (L) | — | 100 | 1 | Powder | −107.6 | 53.76 / 53.41 | 5.95 / 5.76 | 14.25 / 14.06 | 3,320 (broad) / 1,630 |
| 6 | " | COOH pyrrolidine | (D) | — | 38 | 1 | Powder | −17.9 | 53.76 / 53.38 | 5.95 / 5.74 | 14.25 / 14.03 | 3,320 (broad) / 1,600 |

Having now fully described the invention, it will be apparent to one of ordinary skill in the art that many changes and modifications can be made thereto without departing from the spirit of the invention as set forth herein.

What is claimed as new and desired to be secured by Letters Patent of the United States is:

1. An $N^2$-arylsulfonyl-L-argininamide of the formula (I) having the D-configuration in the carbon atom to which the carboxyl group or the ester thereof is attached:

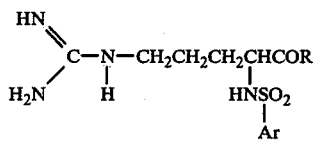

or a pharmaceutically acceptable salt thereof, wherein R is

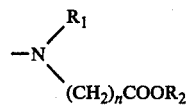

wherein $R_1$ is $C_2$–$C_{10}$ carboxyalkyl, $C_3$–$C_{10}$ alkoxycarbonylalkyl or $C_8$–$C_{15}$ α-carboxyaralkyl; $R_2$ is hydrogen, $C_1$–$C_{10}$ alkyl, $C_6$–$C_{10}$ aryl, $C_7$–$C_{12}$ aralkyl or 5-indanyl; and $n$ is an integer of 1, 2 or 3,

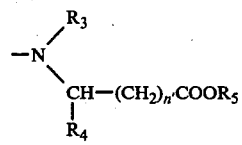

wherein $R_3$ is $C_2$–$C_{10}$ carboxyalkyl, $C_3$–$C_{10}$ alkoxycarbonylalkyl or $C_8$–$C_{15}$ α-carboxyaralkyl; $R_4$ is $C_1$–$C_{10}$ alkyl, phenyl optionally substituted with at least one $C_1$–$C_5$ alkyl, $C_1$–$C_5$ alkoxy, or mixtures thereof, $C_7$–$C_{12}$ aralkyl, or ring substituted benzyl wherein said substituent is $C_1$–$C_5$ alkyl or $C_1$–$C_5$ alkoxy; $R_5$ is hydrogen, $C_1$–$C_{10}$ alkyl, $C_6$–$C_{10}$ aryl, $C_7$–$C_{12}$ aralkyl or 5-indanyl; and $n'$ is an integer of 0, 1 or 2,

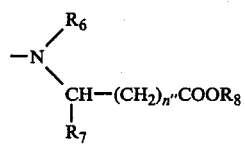

wherein $R_6$ is hydrogen, $C_1$–$C_{10}$ alkyl, $C_3$–$C_{10}$ alkenyl, $C_3$–$C_{10}$ alkynyl, $C_2$–$C_{10}$ alkoxyalkyl, $C_2$–$C_{10}$ alkylthioalkyl, $C_2$–$C_{10}$ alkylsulfinylalkyl, $C_1$–$C_{10}$ hydroxyalkyl, $C_3$–$C_{10}$ alkylcarbonylalkyl, $C_1$–$C_{10}$ haloalkyl, $C_7$–$C_{15}$ aralkyl, $C_3$–$C_{10}$ cycloalkyl, $C_4$–$C_{10}$ cycloalkylalkyl, furfuryl, tetrahydrofurfuryl optionally substituted with at least one $C_1$–$C_5$ alkyl, $C_1$–$C_5$ alkoxy or mixtures thereof, 3-furylmethyl, tetrahydro-3-furylmethyl optionally substituted with at least one $C_1$–$C_5$ alkyl, $C_1$–$C_5$ alkoxy or mixtures thereof, tetrahydro-2 (3 or 4)-pyranylmethyl optionally substituted with at least one $C_1$–$C_5$ alkyl, $C_1$–$C_5$ alkoxy or mixtures thereof, 1,4-dioxa-2-cyclohexylmethyl optionally substituted with one or more $C_1$–$C_5$ alkyl, $C_1$–$C_5$ alkoxy or mixtures thereof, 2-thenyl, 3-thenyl, tetrahydro-2-thenyl optionally substituted with at least one $C_1$–$C_5$ alkyl, $C_1$–$C_5$ alkoxy or mixtures thereof, or tetrahydro-3-thenyl; $R_7$ is carboxyl or $C_2$–$C_{10}$ alkoxycarbonyl; $R_8$ is hydrogen, $C_1$–$C_{10}$ alkyl, $C_6$–$C_{10}$ aryl, $C_7$–$C_{12}$ aralkyl or 5-indanyl; and $n''$ is an integer of 0, 1 or 2,

wherein $R_9$ is —$COOR_{11}$ wherein $R_{11}$ is hydrogen, $C_1$–$C_{10}$ alkyl, $C_6$–$C_{10}$ aryl, $C_7$–$C_{12}$ aralkyl or 5-indanyl; each $R_{10}$ independently is hydrogen, $C_1$–$C_{10}$ alkyl, phenyl, $C_1$–$C_5$ alkoxy, $C_2$–$C_6$ alkoxycarbonyl or carboxy; $m$ is an integer of 1 to 4; $R_9$ is substituted at the 2 or 3-position; and $R_{10}$ can be substituted at the 2, 3, 4, 5 or 6-position,

optionally substituted with at least one $C_1$–$C_5$ alkyl, $C_1$–$C_5$ alkoxy or mixtures thereof wherein $R_{12}$ is hydrogen, $C_1$–$C_{10}$ alkyl, $C_6$–$C_{10}$ aryl, $C_7$–$C_{12}$ aralkyl or 5-indanyl; and $r$ is an integer of 1, 3, 4, 5 or 6,

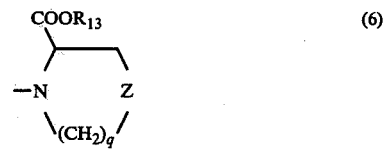

wherein $R_{13}$ is hydrogen, $C_1$–$C_{10}$ alkyl, $C_6$–$C_{10}$ aryl, $C_7$–$C_{12}$ aralkyl or 5-indanyl; Z is oxy, thio or sulfinyl; and $q$ is an integer of 0 or 1, or 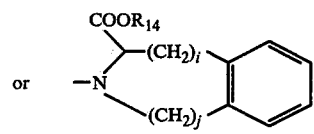

wherein $R_{14}$ is hydrogen, $C_1$–$C_{10}$ alkyl, $C_6$–$C_{10}$ aryl, $C_7$–$C_{12}$ aralkyl or 5-indanyl; $i$ is an integer of 0, 1 or 2; $j$ is an integer of 0, 1 or 2; and the sum of $i + j$ is an integer of 1 or 2; and Ar is a phenyl, naphthyl, naphthoquinonyl, anthryl, phenanthryl, pentalenyl, heptalenyl, azulenyl, biphenylenyl, as-indacenyl, S-indacenyl, acenaphthylenyl, phenylcarbonylphenyl, phenoxyphenyl, benzofuranyl, isobenzofuranyl, benzo(b)-thienyl, isobenzothienyl, oxanthrenyl, thianthrenyl, dibenzofuranyl, dibenzothienyl, phenoxathiinyl, indolyl, 1H-indazolyl, quinolyl, isoquinolyl, phthalazinyl, 1,8-naphthyridinyl, quinoxalinyl, quinazolinyl, cinnolinyl, carbazolyl, acridinyl, phenazinyl, phenothiazinyl, phenoxazinyl or benzimidazolyl group each of which is unsubstituted or substituted with one or more groups selected from the group consisting of halo, nitro, cyano, hydroxy, $C_1$–$C_{10}$ alkyl, $C_1$–$C_{10}$ alkoxy, $C_2$–$C_{20}$ dialkylamino, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl, and phenyl optionally substituted with at least one hydroxy, $C_1$–$C_5$ alkoxy or mixtures thereof, or a $C_9$–$C_{16}$ cycloalkylphenyl, $C_{10}$–$C_{18}$ cycloalkylalkylphenyl, $C_9$–$C_{16}$ cycloalkoxyphenyl, $C_9$–$C_{16}$ cycloalkylthiophenyl, 5,6,7,8-tetrahydronaphthyl, $C_7$–$C_{12}$ aralkyl, 9,10-dihydroanthryl, 5,6,7,8-tetrahydroanthryl, 9,10-dihydrophenanthryl, 1,2,3,4,5,6,7,8-octahydrophenanthryl, indenyl, indanyl, fluorenyl, acenaphthenyl, phenylthiophenyl, 1,2-methylenedioxyphenyl, 1,2-ethylenedioxyphenyl, chromanyl, isochromanyl, 2,3-dihydrobenzofuranyl, 1,3-dihydroisobenzofuranyl, 2,3-ethylenedioxynaphthyl, xanthenyl, thioxanthenyl, 1,2-trimethylenedioxyphenyl, 2H-chromenyl, 3,4-dehydro-1-isochromanyl, 4H-chromenyl, indolinyl, isoindolinyl, 1,2,3,4-tetrahydroquinolyl, or 1,2,3,4-tetrahydroisoquinolyl group each of which is unsubstituted or substituted with one or more groups selected from the group consisting of halo, nitro, cyano, hydroxy, $C_1$–$C_{10}$ alkyl, $C_1$–$C_{10}$ alkoxy, $C_2$–$C_{20}$ dialkylamino, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl, oxo and phenyl optionally substituted with at least one hydroxy, $C_1$–$C_5$ alkoxy or mixtures thereof.

2. The compound of claim 1 wherein R is

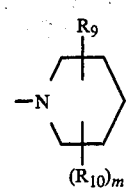

(1)

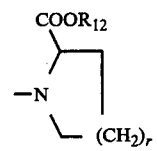

(2)

wherein $R_9$ is —$COOR_{11}$ wherein $R_{11}$ is hydrogen, $C_1$–$C_{10}$ alkyl, $C_6$–$C_{10}$ aryl, $C_7$–$C_{12}$ aralkyl or 5-indanyl; each $R_{10}$ independently is hydrogen, $C_1$–$C_{10}$ alkyl, phenyl, $C_1$–$C_5$ alkoxy, $C_2$–$C_6$ alkoxycarbonyl or carboxy; $m$ is an integer of 1 to 4; $R_9$ is substituted at the 2 or 3-position; and $R_{10}$ can be substituted at the 2, 3, 4, 5 or 6-position, or optionally substituted with at least one $C_1$–$C_5$ alkyl, $C_1$–$C_5$ alkoxy or mixtures thereof wherein $R_{12}$ is hydrogen, $C_1$–$C_{10}$ alkyl, $C_6$–$C_{10}$ aryl, $C_7$–$C_{12}$ aralkyl or 5-indanyl; and $r$ is an integer of 1, 3, 4, 5 or 6.

3. The compound of claim 1 wherein Ar is a phenyl or naphthyl group substituted with at least one substituent selected from the group consisting of $C_1$–$C_5$ alkyl and $C_1$–$C_5$ alkoxy.

4. A method of inhibiting activity and suppressing activation of thrombin in vivo which comprises administering a mammal a pharmaceutically effective amount of a compound of claim 1.

* * * * *